US007666982B2

(12) United States Patent
Okochi et al.

(10) Patent No.: US 7,666,982 B2
(45) Date of Patent: Feb. 23, 2010

(54) NOTCH-ORIGIN POLYPEPTIDES AND BIOMARKERS AND REAGENTS USING THE SAME

(76) Inventors: Masayasu Okochi, c/o Division of Psychiatry and Behavioral Proteomics, Department of Post-Genomics and Diseases, Course of Advanced Medicine, Graduate School of Medicine, Osaka University, D3,-2-2, Yamadaoka, Suita-shi, Osaka 565-0871 (JP); Masatoshi Takeda, c/o Division of Psychiatry and Behavioral Proteomics, Department of Post-Genomics and Diseases, Course of Advanced Medicine, Graduate School of Medicine, Osaka University, D3, 2-2, Yamadaoka, Suita-shi, Osaka 565-0871 (JP)

( * ) Notice: Subject to any disclaimer, the term of this patent is extended or adjusted under 35 U.S.C. 154(b) by 546 days.

(21) Appl. No.: 10/521,691

(22) PCT Filed: Jul. 17, 2003

(86) PCT No.: PCT/JP03/09059

§ 371 (c)(1),
(2), (4) Date: Aug. 31, 2005

(87) PCT Pub. No.: WO2004/009617

PCT Pub. Date: Jan. 29, 2004

(65) Prior Publication Data

US 2006/0166311 A1 Jul. 27, 2006

(30) Foreign Application Priority Data

Jul. 18, 2002 (JP) ............................. 2002-210040

(51) Int. Cl.
C07K 7/08 (2006.01)
C07K 14/435 (2006.01)
(52) U.S. Cl. .................. 530/324; 530/325; 530/326
(58) Field of Classification Search .................. None
See application file for complete search history.

(56) References Cited

FOREIGN PATENT DOCUMENTS

WO 01/75435 10/2001
WO WO -01/75435 A2 * 11/2001

OTHER PUBLICATIONS

Okochi et al. Presenilins mediatea dual intramembranous gamma-secretase cleavage of Notch-1. EMBO J 21(20): 5408-5416, 2002.*

(Continued)

*Primary Examiner*—Bridget E Bunner
(74) *Attorney, Agent, or Firm*—Hamre, Schumann, Mueller & Larson, P.C.

(57) ABSTRACT

It is intended to provide extracellular markers whereby Notch signal transduction can be detected. Polypeptides (Nβ), which are novel peptides originating in Notch protein and released form cells in the step of the nuclear migration of NICH (Notch intracellular cytoplasmic domain) due to the extracellular digestion and the subsequent protein digestion in the membrane during a series of the Notch protein digestion, are referred to as markers. These peptides (Nβ) are released from the cells in proportion to the Notch signal depending on presenilin. By detecting these peptides, the Notch signal transduction, cell differentiation, cell tumorigenesis, apoptosis, Alzheimer's disease, etc. can be monitored.

1 Claim, 11 Drawing Sheets

OTHER PUBLICATIONS

Lammich et al. Presenilin-dependent intramembrane proteolysis of CD44 leads to the liberation of its intracellular domain and the secretion of an AB-like peptide. J Biol Chem 277 (47): 44754-44759, 2002.*

Zhang et al. Proteolysis of chimeric B-amyloid precursor proteins containing the notch transmembrane domain yields B-like peptides. J Biol Chem 277(17): 15069-15075, 2002.*

Okochi et al. Secretion of the Notch-1 AB-like peptide during notch signaling. J Biol Chem 281(12): 7890-7898, 2006.*

Mumm et al. A ligand-induced extracellular cleavage regulates gamma-secretase-like proteolytic activation of notch1. Mol Cell 5: 197-206, 2000.*

Genbank Accession No. Q01705, Nov. 1, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Harper et al. Notch signaling in development and disease. Clin Genet 64: 461-472, 2003.*

Ellisen et al. TAN-1, the human homolog of the Drosophila Notch gene, is broken by chromosomal translocations in T lymphoblastic neoplasms. Cell 65: 649-661, 1991.*

Bash et al. Rel/NF-KB can trigger the Notch signaling pathway by inducing the expression of Jagged1, a ligand for Notch receptors. Embo J 18(10): 2803-2811, 1999.*

Kishi, et al., "Murine homologs of *deltex* define a novel gene family involved in vertebrate Notch signaling and neurogenesis", Int. J. Devl. Neuroscience 19 (2001) 21-35, XP-002356194.

Murphy, et al., "γ-Secretase, Evidence for Multiple Proteolytic Activities and Influence of Membrane Positioning of Substrate on Generation of Amyloid β Peptides of Varying Length", The Journal of Biological Chemistry, vol. 274, No. 17, Apr. 1999, pp. 11914-11923, XP-002254470.

Mumm, et al., "Notch Signaling: From the Outside In", Developmental Biology 228, 151-165 (2000), XP-002264707.

Feldmen et al. "A carboxy-terminal deletion mutant of NotchI accelerates lymphoid oncogenesis in E2A-PBX1 transgenic mice". *Blood*, vol. 96, No. 5, pp. 1906-1913 (Sep. 2000).

Schroeter et al. "Notch-1 signaling requires ligand-induced proteolytic release of intracellular domain". *Letters to Nature*, vol. 393, pp. 382-386 (May 1998).

Wild-Bode et al. "Intracellular generation and accumulation of amyloid β-peptide terminating at amino acid 42". *The Journal of Biological Chemistry*, vol. 272, No. 26, pp. 16085-16088 (Jun. 1997).

Okochi et al. "A loss of function mutant of the presenilin homologue SEL-12 undergoes aberrant endoproteolysis in Caenorhabditis elegans and increases Aβ42 generation in human cells". *The Journal of Biological Chemistry*, vol. 275, No. 52, pp. 40925-40932 (Dec. 2000).

Kulic et al. "Separation of presenilin function in amyloid β-peptide generation and endoproteolysis of notch". *Proc. National Academy Sciences, USA*, vol. 97, No. 11, pp. 5913-5918 (May 2000).

Wolfe et al. "Two transmembrane aspartates in presenilin-1 required for presenilin endoproteolysis and γ-secretase activity". *Letters to Nature*, vol. 398, pp. 513-517 (Apr. 1999).

Sastre et al. "Presenilin-dependent γ-secretase processing of β-amyloid precursor protein at a site corresponding to the S3 cleavage of notch". *EMBO Reports*, vol. 2 No. 9, pp. 835-841 (2001).

Okochi et al. "Presenilins mediate a dual intramembranous γ-secretase cleavage of Notch-1". *The EMBO Journal*, vol. 21, No. 20, pp. 5408-5416 (2002).

Merlos-Suarex et al. "Pro-tumor necrosis factor-α processing activity is tightly controlled by a component that does not affect notch processing". *The Journal of Biological Chemistry*, vol. 273, No. 38, pp. 24955-24962 (Sep. 1998).

Schlondorff et al. "Metalloprotease-disintegrins: modular proteins capable of promoting cell-cell interactions and triggering signals by protein-ectodomain shedding". *Journal of Cell Science*, vol. 112, pp. 3603-3617 (1999).

Chan et al. "Roles for proteolysis and trafficking in notch maturation and signal transduction". *Cell*, vol. 94, pp. 423-426 (Aug. 1998).

Brou et al. "A novel proteolytic cleavage involved in notch signaling: The role of the disintegrin-metalloprotease TACE". *Molecular Cell*, vol. 5, pp. 206-217 (2000).

* cited by examiner

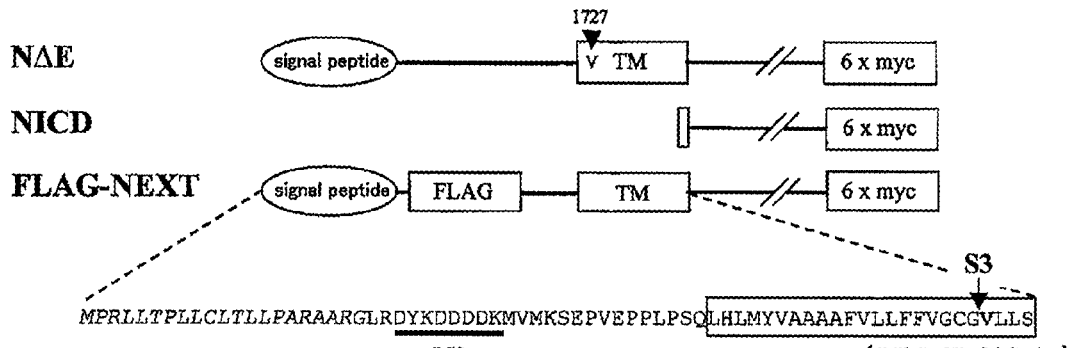
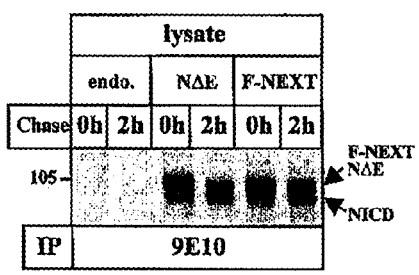
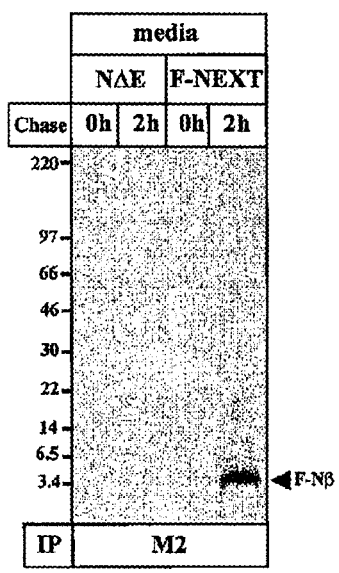
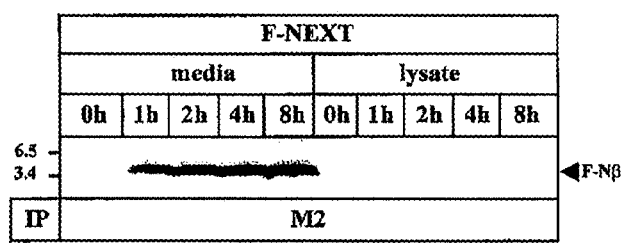
FIG. 1A
FIG. 1B
FIG. 1C

FIG.4A

| | TM | SEQ ID NOS: | |
|---|---|---|---|
| N-LRDYKDDDDKMVMKSEPVEPPLPSQ | LHLMYVAAAAFVLLFFVGCG$^{1743}$-C | 26 | (M.W. 5057.67) |
| N-LRDYKDDDDKMVMKSEPVEPPLPSQ | LHLMYVAAAAFVLLFFVGCG$^{1736}$-C | 27 | (M.W. 4333.81) |
| N-LRDYKDDDDKMVMKSEPVEPPLPSQ | LHLMYVAAAAAFVLLFFVL$^{1735}$-C | 28 | (M.W. 4220.66) |
| N-LRDYKDDDDKMVMKSEPVEPPLPSQ | LHLMYVAAAAAFVLLFFVL$^{1734}$-C | 29 | (M.W. 4121.53) |
| N-LRDYKDDDDKMVMKSEPVEPPLPSQ | LHLMYVAAAAAF$^{1734}$-C | 30 | (M.W. 3974.36) |
| N-LRDYKDDDDKMVMKSEPVEPPLPSQ | LHLMYVAAAAA$^{1733}$-C | 31 | (M.W. 4045.45) |
| N-RGLRDYKDDDDKMVMKSEPVEPPLPSQ | LHLMYVAA$^{1731}$-C | 32 | (M.W. 3832.22) |
| N-LRDYKDDDDKMVMKSEPVEPPLPSQ | LHLMYVAA$^{1731}$-C | 33 | (M.W. 3562.89) |
| N-DYKDDDDKMVMKSEPVEPPLPSQ | LHLMYVAA$^{1731}$-C | 34 | (M.W. 3761.15) |
| N-LRDYKDDDDKMVMKSEPVEPPLPSQ | LHLMYVA$^{1730}$-C | 35 | (M.W. 3590.95) |
| N-LRDYKDDDDKMVMKSEPVEPPLPSQ | LHLMY$^{1728}$-C | 36 | (M.W. 3427.78) |
| N-LRDYKDDDDKMVMKSEPVEPPLPSQ | LHLM$^{1727}$-C | | |

FIG.4B

| | TM | SEQ ID NOS: |
|---|---|---|
| mNotch-1 | LHLMYVAA▼AAFVLLFFVGCG---▼VLL | 37 |
| hNotch-1 | LHFMYVAA--AAFVLLFFVGCG---VLL | 38 |
| mNotch-2 | --LLYLLA-VAVVIILFFIILG-VIMA | 39 |
| hNotch-2 | --LLYLLA-VAVVIILFILLG-VIMA | 40 |
| mNotch-3 | --LLPLIV-AGAVFLLIIFILG-VMVA | 41 |
| hNotch-3 | --LLPLIV-AGAVLLLIVILVLG-VMVA | 42 |
| mNotch-4 | --ILCSPV-VG-VLILLALGALL-VLQLI | 43 |
| hNotch-4 | --VLCSPV-AG-VILLALGALL-VLQLI | 44 |
| hβAPP | GAIIGLMVGGVV▼IATVI-VITTL▼VML | 45 |

LHLMYVAA▼AAFVLLFFVGCG▼V₁₇₄₄LLS (SEQ ID NO:51)

...LHLMYVAAAAFVLLFFVGCGV₁₇₄₄LLS... (SEQ ID NO:52)

...LHLMYVAAAAFVLLFFVGCGG₁₇₄₄LLS... (SEQ ID NO:53)

...LHLMYVAAAAFVLLFFVGCGL₁₇₄₄LLS... (SEQ ID NO:54)

SEQUENCE LISTING

```
<160> NUMBER OF SEQ ID NOS: 57

<210> SEQ ID NO 1
<211> LENGTH: 21
<212> TYPE: PRT
<213> ORGANISM: mouse

<400> SEQUENCE: 1

Val Lys Ser Glu Pro Val Glu Pro Pro Leu Pro Ser Gln Leu His Leu
1               5                   10                  15

Met Tyr Val Ala Ala
            20

<210> SEQ ID NO 2
<211> LENGTH: 17
<212> TYPE: PRT
<213> ORGANISM: mouse

<400> SEQUENCE: 2

Val Lys Ser Glu Pro Val Glu Pro Pro Leu Pro Ser Gln Leu His Leu
1               5                   10                  15

Met

<210> SEQ ID NO 3
<211> LENGTH: 18
<212> TYPE: PRT
<213> ORGANISM: mouse
```

```
<400> SEQUENCE: 3

Val Lys Ser Glu Pro Val Glu Pro Pro Leu Pro Ser Gln Leu His Leu
1               5                   10                  15

Met Tyr

<210> SEQ ID NO 4
<211> LENGTH: 20
<212> TYPE: PRT
<213> ORGANISM: mouse

<400> SEQUENCE: 4

Val Lys Ser Glu Pro Val Glu Pro Pro Leu Pro Ser Gln Leu His Leu
1               5                   10                  15

Met Tyr Val Ala
            20

<210> SEQ ID NO 5
<211> LENGTH: 22
<212> TYPE: PRT
<213> ORGANISM: mouse

<400> SEQUENCE: 5

Val Lys Ser Glu Pro Val Glu Pro Pro Leu Pro Ser Gln Leu His Leu
1               5                   10                  15

Met Tyr Val Ala Ala Ala
            20

<210> SEQ ID NO 6
<211> LENGTH: 23
<212> TYPE: PRT
<213> ORGANISM: mouse

<400> SEQUENCE: 6

Val Lys Ser Glu Pro Val Glu Pro Pro Leu Pro Ser Gln Leu His Leu
1               5                   10                  15

Met Tyr Val Ala Ala Ala Ala
            20

<210> SEQ ID NO 7
<211> LENGTH: 24
<212> TYPE: PRT
<213> ORGANISM: mouse

<400> SEQUENCE: 7

Val Lys Ser Glu Pro Val Glu Pro Pro Leu Pro Ser Gln Leu His Leu
1               5                   10                  15

Met Tyr Val Ala Ala Ala Ala Phe
            20

<210> SEQ ID NO 8
<211> LENGTH: 25
<212> TYPE: PRT
<213> ORGANISM: mouse

<400> SEQUENCE: 8

Val Lys Ser Glu Pro Val Glu Pro Pro Leu Pro Ser Gln Leu His Leu
1               5                   10                  15

Met Tyr Val Ala Ala Ala Ala Phe Val
            20                  25
```

-continued

<210> SEQ ID NO 9
<211> LENGTH: 26
<212> TYPE: PRT
<213> ORGANISM: mouse

<400> SEQUENCE: 9

Val Lys Ser Glu Pro Val Glu Pro Pro Leu Pro Ser Gln Leu His Leu
1               5                   10                  15

Met Tyr Val Ala Ala Ala Ala Phe Val Leu
            20                  25

<210> SEQ ID NO 10
<211> LENGTH: 17
<212> TYPE: PRT
<213> ORGANISM: human

<400> SEQUENCE: 10

Val Gln Ser Glu Thr Val Glu Pro Pro Pro Ala Gln Leu His Phe
1               5                   10                  15

Met

<210> SEQ ID NO 11
<211> LENGTH: 18
<212> TYPE: PRT
<213> ORGANISM: human

<400> SEQUENCE: 11

Val Gln Ser Glu Thr Val Glu Pro Pro Pro Ala Gln Leu His Phe
1               5                   10                  15

Met Tyr

<210> SEQ ID NO 12
<211> LENGTH: 20
<212> TYPE: PRT
<213> ORGANISM: human

<400> SEQUENCE: 12

Val Gln Ser Glu Thr Val Glu Pro Pro Pro Ala Gln Leu His Phe
1               5                   10                  15

Met Tyr Val Ala
            20

<210> SEQ ID NO 13
<211> LENGTH: 21
<212> TYPE: PRT
<213> ORGANISM: human

<400> SEQUENCE: 13

Val Gln Ser Glu Thr Val Glu Pro Pro Pro Ala Gln Leu His Phe
1               5                   10                  15

Met Tyr Val Ala Ala
            20

<210> SEQ ID NO 14
<211> LENGTH: 22
<212> TYPE: PRT
<213> ORGANISM: human

-continued

<400> SEQUENCE: 14

Val Gln Ser Glu Thr Val Glu Pro Pro Pro Ala Gln Leu His Phe
1               5                   10                  15

Met Tyr Val Ala Ala Ala
            20

<210> SEQ ID NO 15
<211> LENGTH: 23
<212> TYPE: PRT
<213> ORGANISM: human

<400> SEQUENCE: 15

Val Gln Ser Glu Thr Val Glu Pro Pro Pro Ala Gln Leu His Phe
1               5                   10                  15

Met Tyr Val Ala Ala Ala Ala
            20

<210> SEQ ID NO 16
<211> LENGTH: 24
<212> TYPE: PRT
<213> ORGANISM: human

<400> SEQUENCE: 16

Val Gln Ser Glu Thr Val Glu Pro Pro Pro Ala Gln Leu His Phe
1               5                   10                  15

Met Tyr Val Ala Ala Ala Ala Phe
            20

<210> SEQ ID NO 17
<211> LENGTH: 25
<212> TYPE: PRT
<213> ORGANISM: human

<400> SEQUENCE: 17

Val Gln Ser Glu Thr Val Glu Pro Pro Pro Ala Gln Leu His Phe
1               5                   10                  15

Met Tyr Val Ala Ala Ala Ala Phe Val
            20                  25

<210> SEQ ID NO 18
<211> LENGTH: 26
<212> TYPE: PRT
<213> ORGANISM: human

<400> SEQUENCE: 18

Val Gln Ser Glu Thr Val Glu Pro Pro Pro Ala Gln Leu His Phe
1               5                   10                  15

Met Tyr Val Ala Ala Ala Ala Phe Val Leu
            20                  25

<210> SEQ ID NO 19
<211> LENGTH: 57
<212> TYPE: DNA
<213> ORGANISM: Artificial
<220> FEATURE:
<223> OTHER INFORMATION: Primer 1 which is derived from mouse Notch-1
      gene for use in site spesific mutagenesis.

<400> SEQUENCE: 19
atcgtcgtcc ttgtagtctc tcaagcctct tgcgccgagc gcgggcagca gcgttag       57

-continued

<210> SEQ ID NO 20
<211> LENGTH: 54
<212> TYPE: DNA
<213> ORGANISM: Artificial
<220> FEATURE:
<223> OTHER INFORMATION: Primer 2 which is derived from mouse Notch-1
      gene for use in site spesific mutagenesis.

<400> SEQUENCE: 20
gacaagatgg tgatgaagag tgagccggtg gagcctccgc tgccctcgca gctg        54

<210> SEQ ID NO 21
<211> LENGTH: 32
<212> TYPE: DNA
<213> ORGANISM: Artificial
<220> FEATURE:
<223> OTHER INFORMATION: Primer 3 which is derived from mouse Notch-1
      gene for use in site spesific mutagenesis.

<400> SEQUENCE: 21
cctcgcagct gcacctcatg tacgtggcag cg                                32

<210> SEQ ID NO 22
<211> LENGTH: 32
<212> TYPE: DNA
<213> ORGANISM: Artificial
<220> FEATURE:
<223> OTHER INFORMATION: Primer 4 which is derived from mouse Notch-1
      gene for use in site spesific mutagenesis.

<400> SEQUENCE: 22
cgctgccacg tacatgaggt gcagctgcga gg                                32

<210> SEQ ID NO 23
<211> LENGTH: 70
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 23

Met Pro Arg Leu Leu Thr Pro Leu Leu Cys Leu Thr Leu Leu Pro Ala
1               5                   10                  15

Arg Ala Ala Arg Gly Leu Arg Asp Tyr Lys Asp Asp Asp Lys Met
            20                  25                  30

Val Met Lys Ser Glu Pro Val Glu Pro Pro Leu Pro Ser Gln Leu His
            35                  40                  45

Leu Met Tyr Val Ala Ala Ala Ala Phe Val Leu Leu Phe Phe Val Gly
        50                  55                  60

Cys Gly Val Leu Leu Ser
65                  70

<210> SEQ ID NO 24
<211> LENGTH: 31
<212> TYPE: PRT
<213> ORGANISM: mouse

<400> SEQUENCE: 24

Leu Pro Ser Gln Leu His Leu Met Tyr Val Ala Ala Ala Ala Phe Val
1               5                   10                  15

Leu Leu Phe Phe Val Gly Cys Gly Val Leu Leu Ser Arg Lys Arg
            20                  25                  30

```
<210> SEQ ID NO 25
<211> LENGTH: 31
<212> TYPE: PRT
<213> ORGANISM: human

<400> SEQUENCE: 25

Gly Ser Asn Lys Gly Ala Ile Ile Gly Leu Met Val Gly Gly Val Val
1               5                   10                  15

Ile Ala Thr Val Ile Val Ile Thr Leu Val Met Leu Lys Lys Lys
            20                  25                  30

<210> SEQ ID NO 26
<211> LENGTH: 45
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 26

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala Ala Ala Phe Val Leu Leu Phe Phe Val Gly Cys Gly
        35                  40                  45

<210> SEQ ID NO 27
<211> LENGTH: 38
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 27

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala Ala Ala Phe Val Leu
        35

<210> SEQ ID NO 28
<211> LENGTH: 37
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 28

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala Ala Ala Phe Val
        35
```

```
<210> SEQ ID NO 29
<211> LENGTH: 36
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 29

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala Ala Ala Phe
        35

<210> SEQ ID NO 30
<211> LENGTH: 35
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 30

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala Ala Ala
        35

<210> SEQ ID NO 31
<211> LENGTH: 35
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 31

Arg Gly Leu Arg Asp Tyr Lys Asp Asp Asp Lys Met Val Met Lys
1               5                   10                  15

Ser Glu Pro Val Glu Pro Pro Leu Pro Ser Gln Leu His Leu Met Tyr
            20                  25                  30

Val Ala Ala
        35

<210> SEQ ID NO 32
<211> LENGTH: 33
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.
```

-continued

```
<400> SEQUENCE: 32

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

Ala

<210> SEQ ID NO 33
<211> LENGTH: 31
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 33

Asp Tyr Lys Asp Asp Asp Lys Met Val Met Lys Ser Glu Pro Val
1               5                   10                  15

Glu Pro Pro Leu Pro Ser Gln Leu His Leu Met Tyr Val Ala Ala
            20                  25                  30

<210> SEQ ID NO 34
<211> LENGTH: 32
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 34

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr Val Ala
            20                  25                  30

<210> SEQ ID NO 35
<211> LENGTH: 30
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.

<400> SEQUENCE: 35

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met Tyr
            20                  25                  30

<210> SEQ ID NO 36
<211> LENGTH: 29
<212> TYPE: PRT
<213> ORGANISM: Artificial
<220> FEATURE:
<223> OTHER INFORMATION: Partial amino acid sequence of F-NEXT which is
      derived from mouse Notch-1 peptide and has FLAG sequence at
      N-terminal region.
```

```
<400> SEQUENCE: 36

Leu Arg Asp Tyr Lys Asp Asp Asp Lys Met Val Met Lys Ser Glu
1               5                   10                  15

Pro Val Glu Pro Pro Leu Pro Ser Gln Leu His Leu Met
            20                  25

<210> SEQ ID NO 37
<211> LENGTH: 23
<212> TYPE: PRT
<213> ORGANISM: mouse

<400> SEQUENCE: 37

Leu His Leu Met Tyr Val Ala Ala Ala Phe Val Leu Leu Phe Phe
1               5                   10                  15

Val Gly Cys Gly Val Leu Leu
            20

<210> SEQ ID NO 38
<211> LENGTH: 23
<212> TYPE: PRT
<213> ORGANISM: human

<400> SEQUENCE: 38

Leu His Phe Met Tyr Val Ala Ala Ala Phe Val Leu Leu Phe Phe
1               5                   10                  15

Val Gly Cys Gly Val Leu Leu
            20

<210> SEQ ID NO 39
<211> LENGTH: 23
<212> TYPE: PRT
<213> ORGANISM: mouse

<400> SEQUENCE: 39

Leu Leu Tyr Leu Leu Ala Val Ala Val Ile Ile Leu Phe Phe Ile
1               5                   10                  15

Leu Leu Gly Val Ile Met Ala
            20

<210> SEQ ID NO 40
<211> LENGTH: 23
<212> TYPE: PRT
<213> ORGANISM: human

<400> SEQUENCE: 40

Leu Leu Tyr Leu Leu Ala Val Ala Val Ile Ile Leu Phe Ile Ile
1               5                   10                  15

Leu Leu Gly Val Ile Met Ala
            20

<210> SEQ ID NO 41
<211> LENGTH: 23
<212> TYPE: PRT
<213> ORGANISM: mouse

<400> SEQUENCE: 41

Leu Leu Pro Leu Leu Val Ala Gly Ala Val Phe Leu Leu Ile Ile Phe
1               5                   10                  15

Ile Leu Gly Val Met Val Ala
            20
```

```
<210> SEQ ID NO 42
<211> LENGTH: 23
<212> TYPE: PRT
<213> ORGANISM: human

<400> SEQUENCE: 42

Leu Leu Pro Leu Leu Val Ala Gly Ala Val Leu Leu Leu Val Ile Leu
1               5                   10                  15

Val Leu Gly Val Met Val Ala
            20

<210> SEQ ID NO 43
<211> LENGTH: 23
<212> TYPE: PRT
<213> ORGANISM: mouse

<400> SEQUENCE: 43

Ile Leu Cys Ser Pro Val Val Gly Val Leu Leu Ala Leu Gly Ala
1               5                   10                  15

Leu Leu Val Leu Gln Leu Ile
            20

<210> SEQ ID NO 44
<211> LENGTH: 23
<212> TYPE: PRT
<213> ORGANISM: human

<400> SEQUENCE: 44

Val Leu Cys Ser Pro Val Ala Gly Val Ile Leu Ala Leu Gly Ala
1               5                   10                  15

Leu Leu Val Leu Gln Leu Ile
            20

<210> SEQ ID NO 45
<211> LENGTH: 24
<212> TYPE: PRT
<213> ORGANISM: human

<400> SEQUENCE: 45

Gly Ala Ile Ile Gly Leu Met Val Gly Gly Val Val Ile Ala Thr Val
1               5                   10                  15

Ile Val Ile Thr Leu Val Met Leu
            20

<210> SEQ ID NO 46
<211> LENGTH: 8
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 46

Leu His Leu Met Tyr Val Ala Ala
1               5

<210> SEQ ID NO 47
<211> LENGTH: 10
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.
```

-continued

```
<400> SEQUENCE: 47

Leu His Leu Met Tyr Val Ala Ala Ala Ala
1               5                   10

<210> SEQ ID NO 48
<211> LENGTH: 11
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 48

Leu His Leu Met Tyr Val Ala Ala Ala Ala Phe
1               5                   10

<210> SEQ ID NO 49
<211> LENGTH: 12
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 49

Leu His Leu Met Tyr Val Ala Ala Ala Ala Phe Val
1               5                   10

<210> SEQ ID NO 50
<211> LENGTH: 28
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 50

Leu His Leu Met Tyr Val Ala Ala Ala Ala Phe Val Leu Leu Phe Phe
1               5                   10                  15

Val Gly Cys Gly Val Leu Leu Ser Arg Lys Arg Arg
            20                  25

<210> SEQ ID NO 51
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 51

Leu His Leu Met Tyr Val Ala Ala Ala Ala Phe Val Leu Leu Phe Phe
1               5                   10                  15

Val Gly Cys Gly Val Leu Leu Ser
            20

<210> SEQ ID NO 52
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.
```

```
<400> SEQUENCE: 52

Leu His Leu Met Tyr Val Ala Ala Ala Ala Phe Val Leu Leu Phe Phe
1               5                   10                  15

Val Gly Cys Gly Val Leu Leu Ser
            20

<210> SEQ ID NO 53
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT(V1744G) which is derived from mouse Notch-1
      peptide.

<400> SEQUENCE: 53

Leu His Leu Met Tyr Val Ala Ala Ala Ala Phe Val Leu Leu Phe Phe
1               5                   10                  15

Val Gly Cys Gly Gly Leu Leu Ser
            20

<210> SEQ ID NO 54
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT(V1744L) which is derived from mouse Notch-1
      peptide.

<400> SEQUENCE: 54

Leu His Leu Met Tyr Val Ala Ala Ala Ala Phe Val Leu Leu Phe Phe
1               5                   10                  15

Val Gly Cys Gly Leu Leu Leu Ser
            20

<210> SEQ ID NO 55
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT which is derived from mouse Notch-1 peptide.

<400> SEQUENCE: 55

Leu His Leu Met Tyr Val Ala Ala Ala Ala Phe Val Leu Leu Phe Phe
1               5                   10                  15

Val Gly Cys Gly Val Leu Leu Ser
            20

<210> SEQ ID NO 56
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT(mutant) which is derived from mouse Notch-1
      peptide.

<400> SEQUENCE: 56

Leu His Leu Met Tyr Val Gly Gly Gly Gly Phe Val Leu Leu Phe Phe
1               5                   10                  15

Val Gly Cys Gly Val Leu Leu Ser
            20
```

```
-continued

<210> SEQ ID NO 57
<211> LENGTH: 24
<212> TYPE: PRT
<213> ORGANISM: Artificial
<220> FEATURE:
<223> OTHER INFORMATION: Partial amino acid sequence of transmembrane
      region of F-NEXT(mutant) which is derived from mouse Notch-1
      peptide.

<400> SEQUENCE: 57

Leu His Leu Met Tyr Val Leu Leu Leu Phe Val Leu Leu Phe Phe
1               5                   10                  15

Val Gly Cys Gly Val Leu Leu Ser
                20
```

NOTCH-ORIGIN POLYPEPTIDES AND BIOMARKERS AND REAGENTS USING THE SAME

TECHNICAL FIELD

The present invention relates to novel polypeptides derived from novel intramembranous endoproteolysis of Notch proteins (hereinafter also referred to collectively as "Notch") and to biomarkers and reagents using the same. In the description of the present invention, the following abbreviations are used for cleavage sites of Notch: S1 for Site-1, S2 for Site-2, S3 for Site-3, and S4 for Site-4. As will be described later, Site-4 (S4) is a novel intramembranous cleavage site discovered by the inventors of the present invention.

BACKGROUND ART

Notch is a type I transmembrane protein present on a cell surface. It contains a repeated EGF-like domain in its extracellular domain and NICD (Notch Intracellular Cytoplasmic Domain), which is a transcription factor containing an ankyrin repeated domain, in its intracellular domain. It has been known that Notch plays a role in intracellular signaling relating to cell differentiation. For example, in the developmental process of a cranial nerve system, some of the cells derived from ectoderm differentiate into neuronal precursor cells (stem cells) and further into nerve cells or glial cells, during which intracellular signaling via Notch is important. The mechanism of the intracellular signaling via Notch is as follows. First, Notch is expressed as a receptor on a Notch signal-receiving cell. During the transport to the cell surface, the Notch undergoes the cleavage at the extracellular domain (S1) by a protease such as furin, and the two Notch fragments resulting from the S1 cleavage are held together through an S-S bond on the cell surface. Next, when a Notch signal-sending cell is present near the Notch signal-receiving cell, a Notch ligand (e.g., Delta, Serrate, or Lag-2, belonging to a DSL family) is expressed on the surface of the Notch signal-sending cell. Under these two conditions, the Notch ligand interacts with the Notch receptor on the cell surface, whereby sequential proteolytic events are induced to trigger signal transduction. More specifically, the Notch is cleaved at a site (S2) close to the cell surface, which triggers the cleavage at a site (S3) that is either inside the cell membrane or in close proximity to the cell membrane inside the cell. NICD, which is the intracellular domain of the Notch resulting from the S3 cleavage, is released to an intracellular space and translocates to the nucleus, where it binds to a CSL family (CPB, SuH, or Lag-1; transcription factor) to regulate the transcription of target genes. Presenilin, which is associated with Alzheimer's disease, is involved in the S3 cleavage.

As described above, Notch plays an extremely important role in intracellular signaling for cell differentiation. Moreover, recent studies have revealed that Notch is involved not only in the differentiation of a cranial nerve system as described above but also in cell tumorigenesis, apoptosis, Alzheimer's disease, etc., which causes Notch to become a focus of attention (see Okochi et al., "Biology of Alzheimer's disease and presenilin", Bunshi Seishin Igaku, Vol. 1, No. 3, 2001; Kageyama et al., "Notch pathway in neural development", Tanpakushitsu Kakusan Koso, Vol. 45, No. 3, 2000; and Brian et al., "A carboxy-terminal deletion mutant of Notch 1 accelerates lymphoid oncogenesis in E2A-PBX1 transgenic mice", Blood, Vol. 96, No. 5, Sep. 1, 2000, pp 1906-1913). Therefore, the detection of Notch signal transduction is extremely important for research and diagnosis of cell differentiation, cell tumorigensis, apoptosis, Alzheimer's disease, etc., and the earlier possible establishment of the technology for detecting Notch signal transduction is being demanded.

DISCLOSURE OF THE INVENTION

Therefore, with the foregoing in mind, it is an object of the present invention to provide a substance that can serve as an extracellular secreted marker for detecting Notch signal transduction.

The inventors of the present invention hypothesized that, during a series of proteolytic events of Notch, a polypeptide remaining in a cell membrane is released to an extracellular space as a result of the cleavage occurring at S3, and decided to examine this hypothesis. This is because, if the polypeptide remaining in the cell membrane is released to an extracellular space, it can serve as a marker for Notch signal transduction. Through a series of studies on Notch signal transduction, the inventors of the present invention found out that a fourth cleavage occurs at a site (in the transmembrane domain) different from the S3 cleavage site and a polypeptide resulting from this fourth cleavage is released to an extracellular space. Based on this finding, the inventors arrived at the present invention.

That is, the novel polypeptide according to the present invention is a polypeptide derived from a Notch protein. In a series of proteolytic events of the Notch protein, the polypeptide is released to an extracellular space when NICD (Notch intracellular cytoplasmic domain) translocates to a nucleus as a result of the intramembranous endoproteolysis that occurs subsequent to the extracellular proteolysis. This polypeptide can be detected by using an antibody or the like, and thus can be used as a marker for detecting Notch signal transduction. Furthermore, since Notch signal transduction is involved in cell differentiation, cell tumorigensis, Alzheimer's disease, apoptosis, etc., the novel polypeptide according to the present invention also can be used as a marker for detecting them. Moreover, as will be described later, there are several types of novel polypeptide according to the present invention with their C-termini being different from each other. Hereinafter, the novel polypeptide according to the present invention is referred to also as "Notch-β(Nβ)". Also, the above-described intramembranous endoproteolysis is not limited to that occurring in a cell membrane but includes that occurring in an organelle membrane.

BRIEF DESCRIPTION OF THE DRAWINGS

FIG. 1A is a schematic illustration of structures of NΔE, FLAG-NEXT (F-NEXT), and NICD. FIGS. 1B and 1C are electrophoretograms showing an example of the production of FLAG-tagged novel polypeptides (Nβs) according to the present invention.

FIG. 4A shows an example of amino acid sequences of the novel polypeptides as a principle part of the present invention. FIG. 4B is a view showing the comparison between intramembranous amino acid sequences of Notch-1 to Notch-4 and that of hβAPP.

BEST MODE FOR CARRYING OUT THE INVENTION

Figure 2B:
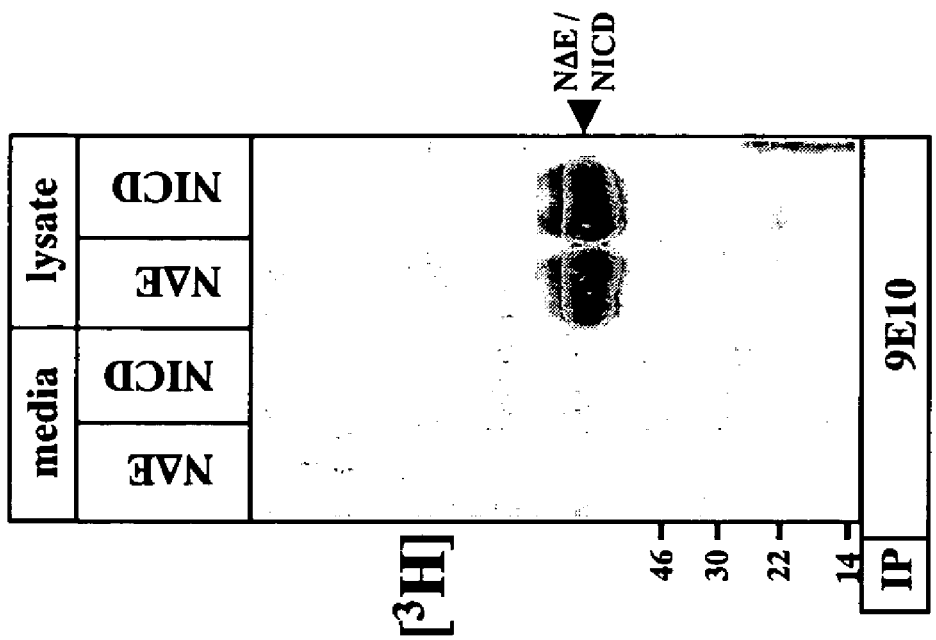
FIGS. 2A and 2B are electrophoretograms showing an example of the production of novel polypeptides (Nβs) according to the present invention.

Hereinafter, the present invention will be described further in detail.

A polypeptide according to the present invention is released to an extracellular space in proportion to Notch signal transduction. Besides, novel proteolysis that occurs immediately before the release of the polypeptide to the extracellular space is presenilin dependent, and inhibition of the presenilin function causes a decrease in the release of the polypeptide of the present invention.

The novel polypeptide according to the present invention is produced and released as a result of the proteolysis (S4 cleavage) of a Notch protein that occurs simultaneously with or either before or after the proteolysis of the Notch protein at a S3 cleavage site. The proteolysis (S4 cleavage) occurs on a N-terminal side with respect to the S3 cleavage site in a transmembrane domain of the Notch protein.

The novel polypeptide (Nβ) according to the present invention is a polypeptide including an amino acid sequence selected from SEQ ID NOS: 1 to 18. In these SEQ ID NOS: 1 to 18, SEQ ID NOS: 1 to 9 represent murine amino acid sequences, while SEQ ID NOS: 10 to 18 represent human amino acid sequences. In the amino acid sequences represented by the SEQ ID NOS: 1 to 18, one or several of the amino acids may be deleted, substituted, or inserted. Polypeptides represented by such amino acid sequences also are derived from Notch proteins, and are released to an extracellular space when NICD translocates to a nucleus as a result of intramembranous endoproteolysis that occurs subsequent to extracellular proteolysis in a series of proteolytic events of the Notch proteins. These polypeptides also are released to an extracellular space in proportion to a Notch signal in a presenilin-dependent manner. It is to be noted that the novel polypeptide according to the present invention may be derived from a living organism or may be synthesized artificially. The living organism is not limited to a particular type, and may be, for instance, a human, a mouse, a rat, a rabbit, a goat, a swine, a bovine, a drosophila, or a nematode. Also, the type of tissue or cell from which the novel polypeptide of the present invention is derived is not particularly limited. More specifically, somatic cells and tissues, such as nerve, marrow, and cancer cells and tissues, may be the source of the polypeptide of the present invention, regardless of whether undifferentiated or differentiated.

A biomarker according to the present invention contains the above-described polypeptide of the present invention. The biomarker of the present invention can be used for detecting Notch signal transduction, cell differentiation, tumor, apoptosis, Alzheimer's disease, or the like. The biomarker of the present invention further may contain other components, or alternatively, it may be the novel polypeptide itself (i.e., the biomarker may contain the novel polypeptide alone). This biomarker can be detected using a reagent containing an antibody that can recognize the novel polypeptide. The antibody that can recognize the novel polypeptide can be prepared by an ordinary method, and may be a monoclonal antibody or a polyclonal antibody. In addition to the antibody that can recognize the novel polypeptide, the reagent further may contain a labeled antibody against this antibody or a labeled antibody that can recognize the novel polypeptide. The labeling can be achieved, for example, by using a fluorescent substance, an enzyme (e.g., an enzyme that acts on a substrate that develops color when reacting with the enzyme), a radioactive substance, or a carrier such as agarose.

A gene according to the present invention is a gene encoding the novel polypeptide of the present invention, and may be DNA or RNA. A vector according to the present invention is a vector containing the above-described gene, and a transformant according to the present invention is a transformant transformed with the above-described vector.

Figure 7:
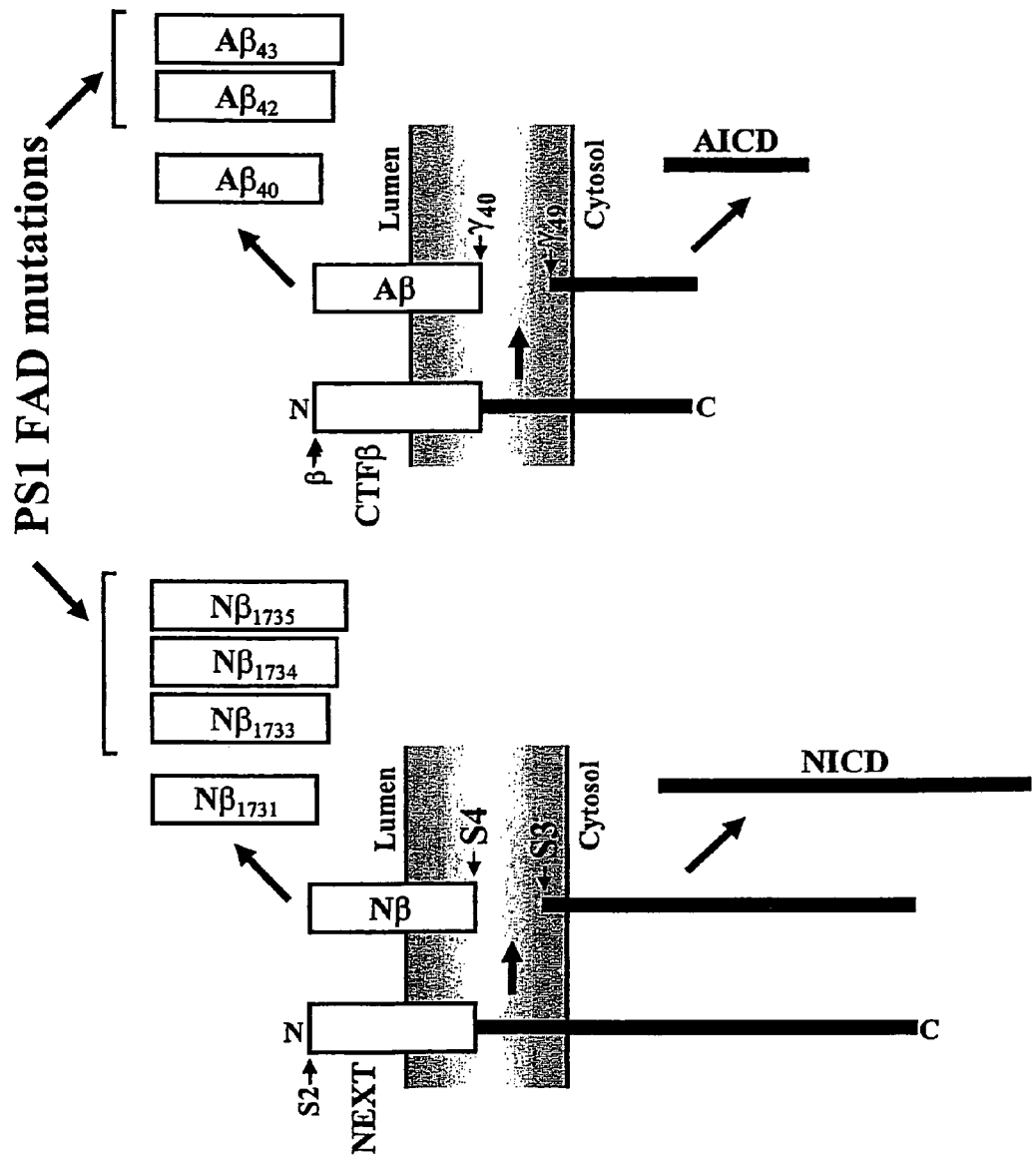
FIG. 7 is a schematic illustration of an example of extracellular release of novel polypeptides (Nβs) according to the present invention and illustrates the C-terminus of the released peptide is changed by Alzheimer's disease pathogenic presenilin mutants.

Next, an example of the extracellular release of the novel polypeptide according to the present invention will be described with reference to the left region of FIG. 7. It is to be noted that the right region of FIG. 7 shows an example of the extracellular release of amyloid-β (Aβ) in Alzheimer's disease. As shown in the left region of FIG. 7, the amino terminus of NEXT (Notch Extracellular Truncation) is produced as a result of extracellular cleavage by TACE (TNFβ-Converting Enzyme). The NEXT resulting from the S2 cleavage then undergoes S3 cleavage, and NICD resulting from the S3 cleavage translocates to the nucleus. Cleavage at S4 (the fourth cleavage site of Notch newly discovered by the inventors of the present invention) occurs simultaneously with or either before or after the S3 cleavage, so that Nβ (a novel polypeptide according to the present invention) is released to an extracellular space.

Next, an example of C-terminus amino acid sequences of novel polypeptides of the present invention will be described with reference to FIG. 4B. FIG. 4B shows sequences near the C-termini of Nβs or fragments released to an extracellular space with regard to 4 types of murine Notch (mNotch-1 to mNotch-4), 4 types of human Notch (hNotch-1 to hNotch-4), and hβAPP. As shown in FIG. 4B, the major S4 cleavage site resides a few amino acid residues closer to the N-terminus with respect to the center of putative transmembrane domain (TM) (indicated by the triangular arrowhead on the left in the drawing). Furthermore, as shown in FIG. 4B, amino acid sequences around the major cleavage site are not conserved in mNotch-1 to mNotch-4, though valine 1743 as the S3 cleavage site is conserved (indicated by the triangular arrowhead on the right in the drawing). Thus, the S4 cleavage site is characterized by its diversity, unlike the S3 cleavage. It is speculated that this diversity might reflect the peculiarity of the mechanism by which S4 secretase recognizes the sequence of the cleavage site.

EXAMPLES

Hereinafter, the present invention will be described by way of examples. Reagents, materials, and experimental procedures used in the respective examples are as follows.

(Reagent)

A γ-Secretase inhibitor, [(2R,4R,5S)-2-Benzyl-5-(Boc-amino)-4-hydroxy-6-phenyl-hexanoyl]-Leu-Phe-NH2, was purchased from Bachem.

(Plasmids)

cDNAs encoding Notch ΔE-M1727V (NΔE) and NICD with C-terminal 6× c-myc tag inserted in pcDNA3 hygro were prepared in the manner described in Schroeter et al. (Schroeter, E. H., Kisslinger, J. A., Kopan, R. (1998), "Notch-1 signalling requires ligand-induced proteolytic release of intracellular domain", Nature, 393, 382-386). The cDNAs were gift from Dr. R. Kopan. N-terminally FLAG-tagged NEXT, i.e., FLAG-NEXT (F-NEXT), was prepared by 2-step site-directed mutagenesis. In the first step, F-NEXT M1727V was produced using the ExSite PCR-Based Site-Directed Mutagenesis Kit (Stratagene). NΔE was used as a template, and the following two primers 1 and 2 were prepared.

```
Primer 1:
5-
P-ATCGTCGTCCTTGTAGTCTCTCAAGCCTCTTGCGCCGAGCGCGGGCA
GCAGCGTTAG-3' (SEQ ID NO: 19)

Primer 2:
5-P-GACAAGATGGTGATGAAGAGTGAGCCGGTGGAGCCTCCGCTGCCCT
CGCAGCTG-3' (SEQ ID NO: 20)
```

In the second step, F-NEXT was prepared by site-directed mutagenesis using Quick Change Site-Directed Mutagenesis Kit (Stratagene). The F-NEXT M1727V was used as a template, and the following two primers 3 and 4 were prepared.

```
Primer 3:   5-CCTCGCAGCTGCACCTCATGTACGTGGCAGCG-3'
(SEQ ID NO:
21)

Primer 4:   5-CGCTGCCACGTACATGAGGTGCAGCTGCGAGG-3'
(SEQ ID NO:
22)
```

Each mutant was sequenced to verify successful mutagenesis.

(Antibodies)

The polyclonal antibody (L652) is an antibody against a polypeptide with the amino acid sequence from V 1722 to G 1743 of human Notch-1 (i.e., the sequence between S2 and S3). The antibody (L652) was produced in the following manner. First, the above-described polypeptide serving as an antigen was provided. This polypeptide is characterized in that it contains a lot of hydrophobic amino acids. On this account, the antibody was produced in the same manner as that used for producing an antibody against the Alzheimer's disease amyloid β-protein. More specifically, the antibody was produced in the following manner. The polypeptide was dissolved in water directly without being conjugated with any carrier protein. After addition of the same volume of 2× phosphate buffer, the polypeptide was emulsified with adjuvant and injected into rabbits (Wild-Bode, C., Yamazaki, T., Capell, A., Leimer, U., Steiner, H., Ihara, Y, Haass, C. (1997), "Intracellular generation and accumulation of amyloid beta-peptide terminating at amino acid 42", J Biol Chem 272, 16085-16088). A monoclonal antibody (9E10) against c-myc and a reagent (M2-agarose) in which a monoclonal antibody against FLAG is covalently bound to agarose were obtained commercially.

(Cell Cultures and Cell Lines)

Human embryonic kidney 293 (K293), N2a and COS cells were cultured in DMEM supplemented with 10% fetal bovine serum, 1% penicillin/streptomycin, and 200 µg/ml zeocin (to select for PS1 expression), and/or 100 µg/ml hygromycin (to select for NΔE and F-NEXT expression). The K293 can stably express wild-type PS1, PS1 L286V, or PS1 D385N (Okochi et al., 2000, Kulic et al., 2000, Wolfe et al., 1999). The transfection with NΔE or F-NEXT was performed by means of a product named Lipofectamine 2000 (Invitrogen).

(Pulse-Chase)

To determine NΔE N-terminal fragment (NTF: Nβ) release from NΔE expressing cells, K293 cells stably transfected with NΔE or NICD were grown to confluence in a 10 cm dish. The cells were then metabolically pulse-labeled for 2 hours with 300 µCi [$^3$H] amino acids (tritiated amino acid mixture, Amersham) in Earle's Balanced Salt Solution supplemented with MEM Vitamine Solution (Gibco) and several cold amino acids, followed by a 6-hour chase by 10% FCS/DMEM. To examine Nβ release, cells expressing F-NEXT were, at first, starved of methinine for 40 min with methionine-free media and then pulse-labeled for 1 hour with 400 µCi [$^{35}$S] amino acid mixture (Redivue Promix, Amersham) in methionine-free DMEM, followed by chasing for various time periods with the chase media containing 10% FCS/DMEM supplemented with excess cold methionine.

(Immunoprecipitation/SDS-PAGE)

At the end of the respective chase periods, the media were collected and put on ice immediately, followed by centrifugation at 3000× g to exclude cell debris. Next, a protease inhibitor cocktail (1:1000; Sigma) and 0.025% of sodium azide were added. The thus-obtained samples were immunoprecipitated with L652 or M2-agarose (Sigma) overnight and then washed three times with RIPA buffer containing 0.1% SDS, 0.5% deoxycholic acid, and 1% TritonX-100, followed by SDS-PAGE using Tris-Tricine 10% to 20% gradient gel (Invitrogen). The cells were scraped in ice-cold PBS, and then harvested by means of 1500×g centrifugation, followed by lysation with 100 µl of 10× RIPA. 900 µl of PBS with a protease inhibitor mix (1:500; Sigma) was then added to the lysed cells. The insoluble fraction was separated by 15000× g centrifugation and the resultant supernatant was used for immunoprecipitation. The samples for immunoprecipitation were pretreated by protein A sepharose (Sigma) and immunoprecipitated with 9E10 or M2 agarose. Next, the washed protein samples were separated by 8% or Tris-Tricine SDS-PAGE. After fixation, the gel was shaken in Amplify Fluorographic Reagent (Amersham), dried, and autoradiographed.

(Immunoprecipitation IMALDI-TOF MS Analysis)

After cells stably expressing the F-NEXT and their derivatives were grown to confluence in a 20 cm dish, the culture media were replaced with fresh 10% FCS/DMEM. After the cells with the fresh conditioned media were cultured for 3 hours in a $CO_2$ incubator, the culture media were collected and immediately put on ice and centrifuged to eliminate cell debris. After supplementation with a protease inhibitor mix (1:1000) and 0.025% sodium azide, the media were immunoprecipitated with M2-agarose for 4 hours at 4° C. The samples were then washed three times for 10 min at 4° C. with an MS wash buffer containing 0.1% n-octylglucoside, 140 mM NaCl, 10 mM Tris (pH 8.0), and 0.025% sodium azide. The samples were then washed once again with 10 mM Tris (pH 8.0) containing 0.025% sodium azide. Peptides bound to the resultant precipitates were eluted with TFA/Acetonitrile/Water (TFA:acetonitorile:water=1:20:20) saturated with α-cyano-4 hydroxy cinnamic acid. The solubilized samples were dried on a stainless plate and subjected to a MALDI-TOF MS analysis. MS peaks were calibrated using angiotensin (Sigma) and insulin β-chain (Sigma).

Example 1

Detection of N-Terminal Fragment (NTF; F-Nβ) of FLAG-NEXT (F-NEXT) in Culture Media FIG. 1A is a schematic illustration of structures of NΔE, NICD, and F-NEXT. As shown in FIG. 1A, in F-NEXT, a signal peptide and also a FLAG sequence and two methionines subsequent to the signal peptide are inserted into the N-terminus of NEXT. The 1727th amino acid residue was not mutated in the F-NEXT. However, in NΔE (murine Notch-1 (mNotch-1)), methionine 1727 was artificially mutated to valine, as indicated by the inverse triangle in FIG. 1A (Schroeter, E. H., Kisslinger, J. A., Kopan, R. (1998), "Notch-1 signalling requires ligand-induced proteolytic release of intracellular domain", Nature, 393, 382-386.). The triangular arrowhead indicates a S3 cleavage site.

Cells stably expressing NΔE or F-NEXT were pulse-labeled for 1 hour with [$^{35}$S] and chased for the time period indicated in FIG. 1B. The resultant cell lysates were immunoprecipitated with 9E10 and analyzed by 8% SDS-PAGE. As shown in the upper panel of FIG. 1B, proteolysis of NΔE (the middle region of the panel) and F-NEXT (the right region of the panel) was observed after a 2-hour chase, which resulted in NICD bands migrating faster than those of NΔE and F-NEXT. With regard to the NICD production efficiency, there was no difference between the cells expressing NΔE and the cells expressing F-NEXT.

Next, the culture media were immunoprecipitated with M2-agarose and analyzed by 8% SDS-PAGE. As shown in the lower panel of FIG. 1B, a band of F-Nβs (an aggregate of novel polypeptide groups according to the present invention) of about 4 kDa was identified only in the 2-hour chased media of the cells stably expressing F-NEXT. The result indicates an entirely new finding that, during the NICD production, an amino terminal fragment on the side opposite to the NICD is secreted into an extracellular space.

F-NEXT expressing cells were pulse-labeled with [$^{35}$S] for 1 hour and chased for the time periods indicated in FIG. 1C. F-Nβs in the media and the lysates were examined by the above-described experimental procedures. As shown FIG. 1C, accumulation of F-Nβs (an aggregate of novel polypeptide groups according to the present invention) in accordance with the extension of chase period was observed in the media, but was hardly detectable in the cell lysates. However, with longer exposure of a film when taking a picture of electrophoresis gel, a F-Nβ band with the same molecular weight (hereinafter referred to as "MW") as in the media was also detectable in the lysates (data not shown).

The results shown in FIGS. 1B and 1C were reproduced when F-NEXT M1727V mutant was used or when CHO, COS, and N2a were used as the expressing cells (data not shown).

Example 2

Detection of N-Terminal Fragment (NTF:Nβ) of NΔE in Culture Media

Figure 2A:
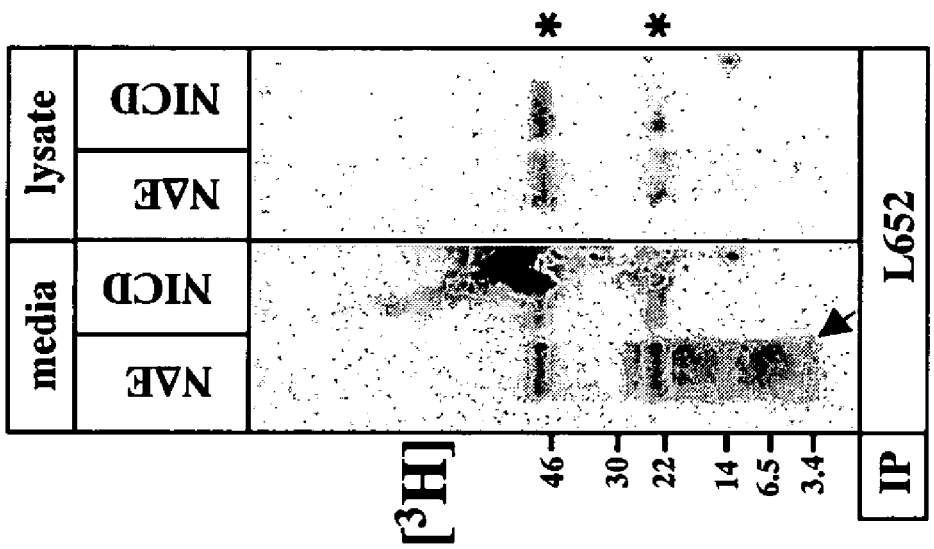

K293 cells stably expressing NΔE or NICD were pulse-labeled with [$^3$H] for 2 hours and chased for 6 hours. Chased media and cell lysates were immunoprecipitated with an antibody L652 against NΔE, and the thus-obtained samples were separated by Tris-Tricine SDS-PAGE. As shown in FIG. 2A, a NΔE NTF band (indicated by the triangular arrowhead) of MW 3 to 4 kDa was detected in the culture media of the NΔE cells, but not from the culture media or cell lysate of the NICD cells. Thus, it was considered that the band shown in FIG. 2A was of wild-type Nβs that were not FLAG-tagged.

The same media and lysates as in the above were immunoprecipitated with an anti-c-myc antibody (9E10). As shown in the lower panel of in FIG. 2B, about 100 kDa bands of NΔE and NICD were detected in the lysates (indicated by the triangular arrowhead), but not in the media. This result suggests that NΔE and NICD were expressed in the respective cells at substantially the same rate.

Example 3

Identification of C-Termini of Nβs Released to Culture Media

Figure 3A:
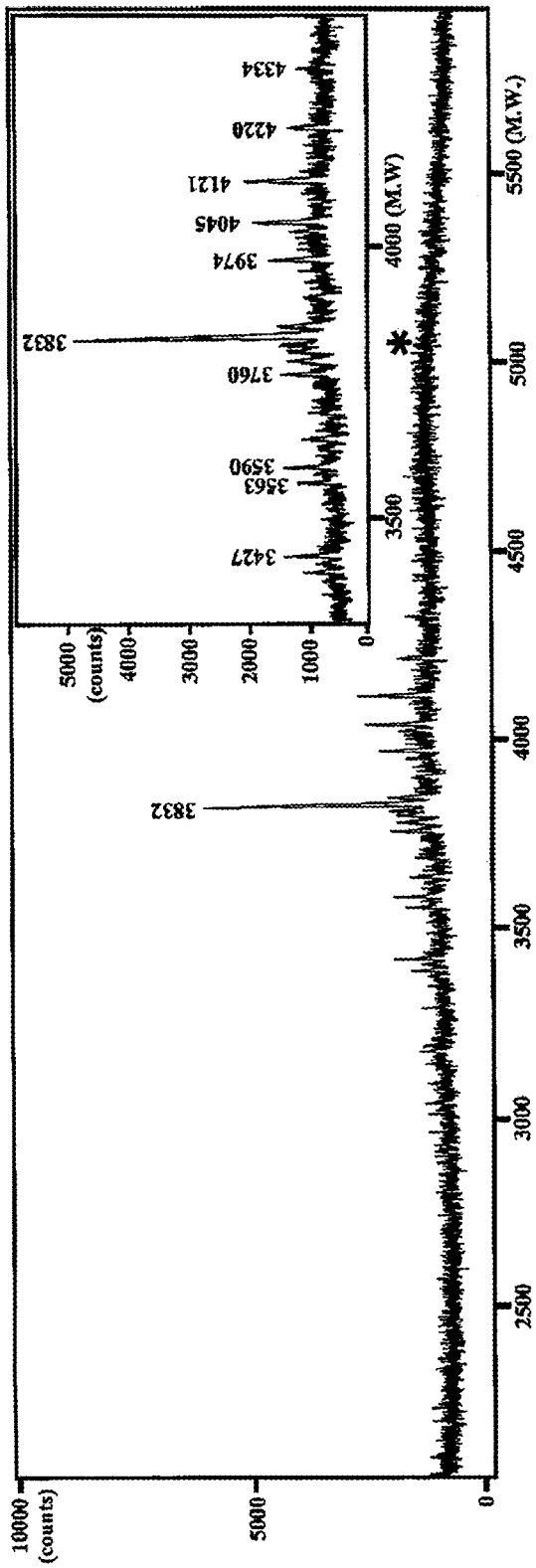
FIG. 3A is a chart showing the result of mass spectroscopy with regard to a group of novel polypeptides according to the present invention.
Figure 3B:
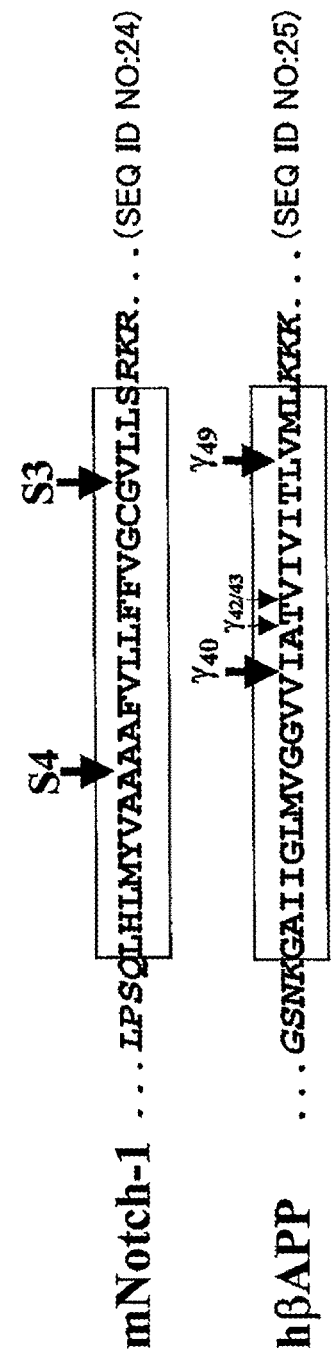
FIG. 3B shows a major site of a novel cleavage (S4 cleavage) of a Notch protein and major cleavage sites of an Alzheimer's disease β-amyloid precursor protein (hβAPP).

FIG. 3B is a schematic illustration of intramembranous cleavage of murine Notch-1 (mNotch-1) and human βAPP (hβAPP). As a result of the intramembranous cleavage of mNotch-1, NICD and Nβ are produced. In the present example, Nβ secretion and a novel cleavage site at the C-terminus of Nβ were confirmed. On the other hand, as a result of the intramembranous cleavage of hβAPP, an intracellular fragment CTFγ50 (Sastre, M., Steiner, H., Fuchs, K., Capell, A., Multhaup, G., Condron, M. M., Teplow, D. B., Haass, C. (2001), "Presenilin-dependent gamma-secretase processing of beta-amyloid precursor protein at a site corresponding to the S3 cleavage of Notch", EMBO Rep. 2, 835-841.) and several types of Aβ fragments are produced.

Culture media of cells stably expressing F-NEXT were immunoprecipitated with M2-agarose, and MW of Nβs were analyzed by means of MALDI-TOF MS according to the above-described experimental procedures. The result is shown in the large graph shown in FIG. 3A. As shown in the graph, multiple peaks were observed around MW 4000, but no significant peaks of MW more than 4500 were identified. The small graph shown in FIG. 3A shows the details of the peaks from MW 3000 to 4500. The same major peaks were identified when CHO, COS and N2a were used as host cells (data not shown). These peaks also were identified when transfected with F-NEXT M1727V mutant (data not shown).

FIG. 4A shows a list of amino acid sequences of Nβs corresponding to the MALDI-TOF MS peaks shown in the small graph of FIG. 3A. The C-terminus of the major Nβ species was alanine 1731. Bold letters indicate an amino acid sequence of the major peak. As shown in FIG. 4A, no peaks of MW around 5060, corresponding to a S3 cleavage site, were identified. From these results, it can be concluded that Nβs are released to an extracellular space and the cleavage site of the proteolysis occurring just before the Nβ release is a novel fourth cleavage site (S4) that is different from the conventionally reported three cleavage sites (S1, S2, and S3).

FIG. 4B shows a list of amino acid sequences of transmembrane domains of human (h) and murine (m) Notch-1 to Notch-4. S1, S2, and S3 cleavages are phenomena common to Notch-1 to Notch-4, and they serve as a common signal transduction mechanism through which Notch proteins, whatever their species, achieve signal transduction. From these facts, it is speculated that S4 cleavage also is a phenomenon common to Notch proteins of all types. As shown in FIG. 4B, the S4 cleavage site is conserved partially, similarly to the S3 cleavage site. From this fact, it is speculated that S4 cleavage is a phenomenon common to Notch-1 to Notch-4.

Example 4

Confirmation of Presenilin (PS) Function Dependence of Extracellular Release of Nβ

Figures 5A, 5B:
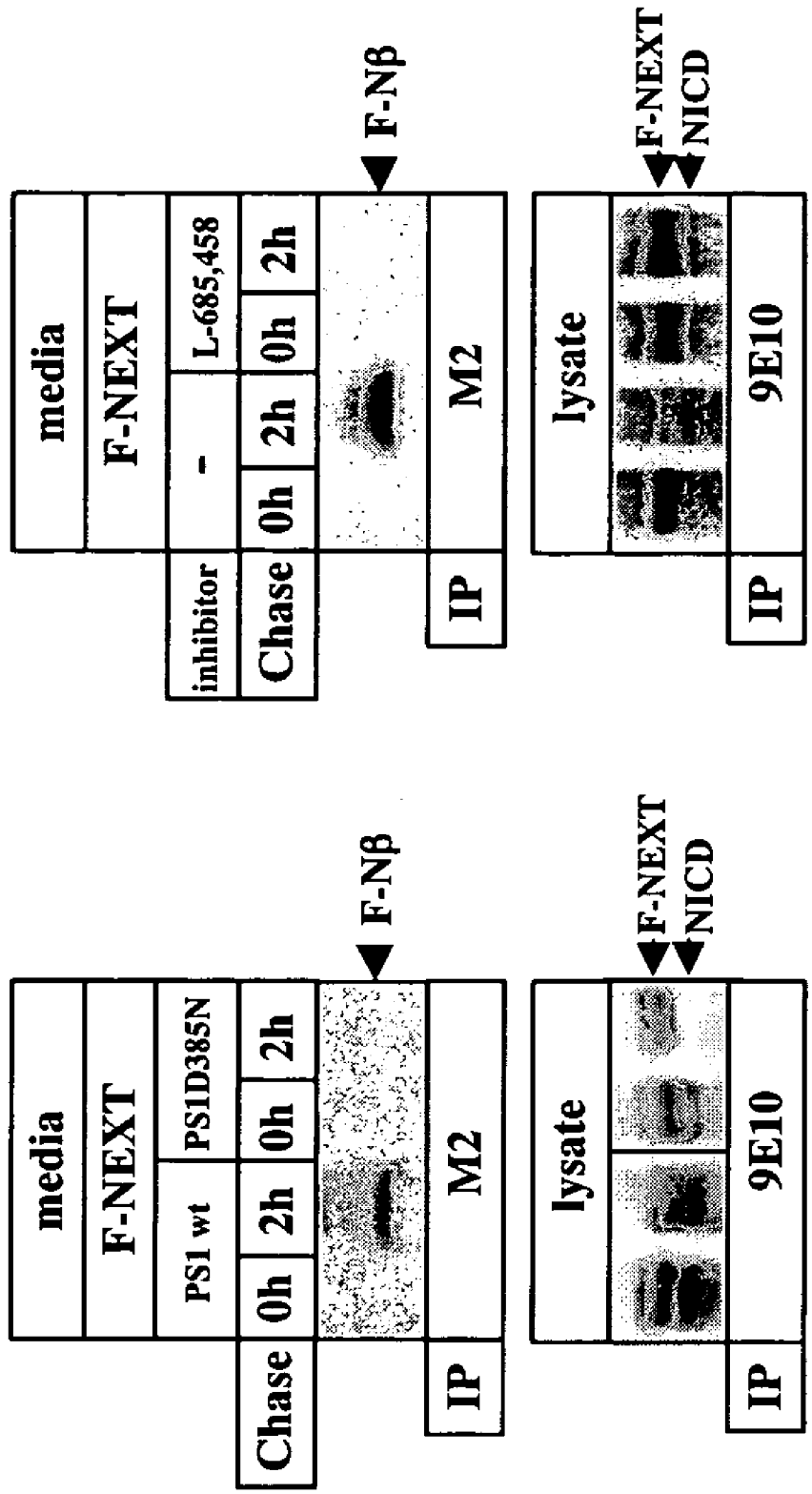
FIGS. 5A and 5B are electrophoretograms showing an example of the effect of inhibition of presenilin (PS) function upon extracellular release of novel polypeptides (Nβs) according to the present invention.

Cells expressing wild-type PS1 or PS1 D385N that is a PS1 dominant negative mutant obtained by artificially causing loss of presenilin function were stably transfected with F-NEXT. An hour pulse with [$^{35}$S] and then a 2-hour chase were performed, and the resulting culture media and lysates were analyzed to determine an Nβ release level from the cells expressing both the PS1 derivative and F-NEXT at the same time. First, the chased media were immunoprecipitated with M2-agarose to detect Nβ release. As shown in the upper panel of FIG. 5A, Nβ release from the PS1 D385N expressing cells decreased drastically as compared with the case of the wild-type PS1 expressing cells. That is, it was confirmed that the S4 cleavage efficiency decreases drastically in the cells expressing the mutant obtained by artificially causing loss of presenilin function. Also, the lysates collected at the same time with the culture media were immunoprecipitated with 9E10. As shown in the lower panel of FIG. 5A, NICD band after the 2-hour chase was hardly visible in the PS1 D385N expressing cells. That is, the report that the S3 cleavage efficiency decreases drastically in the cells expressing the mutant obtained by artificially causing loss of presenilin function was reproduced at the same time.

Next, cells stably expressing F-NEXT were pulse-labeled for 1 hour and chased for 2 hours with or without a γ-secretase inhibitor (L685,458) that is designed to bind the active center of presenilin. More specifically, 1 μM of L685,458 was added to the culture media 2 hours before methionine starvation. During the pulse-chase period, every medium used contained the same concentration of L685,458. The chased media were immunoprecipitated with M2-agarose to detect Nβ release. As shown in the upper panel of FIG. 5B, Nβ release from the cells treated with the γ-secretase inhibitor decreased drastically. Also, the corresponding lysates were immunoprecipitated with 9E10. As shown in the lower panel of FIG. 5B, the NICD band after the 2-hour chase period was hardly visible due to inhibition of S3 cleavage. From these results, it can be said that the Nβ release to an extracellular space is caused by presenilin-dependent proteolysis, and hence, inhibition of the presenilin function results in the inhibition of S4 cleavage and Nβ release that occurs subsequent to the S4 cleavage.

Example 5

Effect of Presenilin (PS) Mutant Associated with Familial Alzheimer's Disease (FAD) upon S4 Cleavage Heretofore, various studies have been made on PS mutation associated with FAD, and an increase in Aβ secretion has been confirmed in every type of FAD pathogenic PS mutant. In the present example, it was confirmed that PS dependent S4 proteolysis also relates to PS mutation associated with FAD.

Figure 6A:
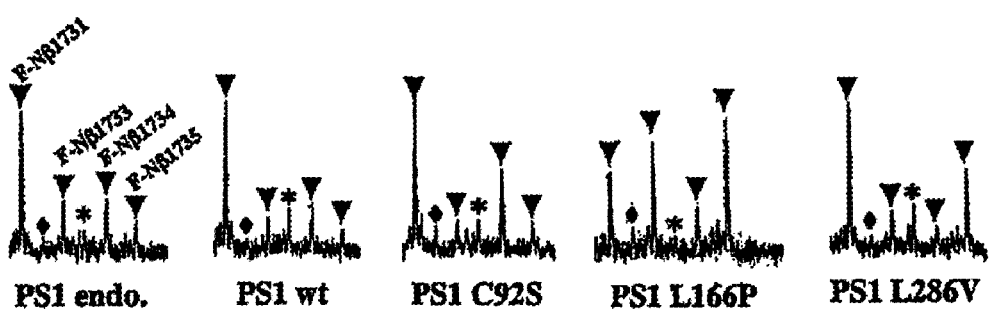
FIG. 6A is a chart showing the result of mass spectroscopy, which shows an example of the effect of Alzheimer's disease pathogenic presenilin mutants upon Nβ release.
Figure 6B:
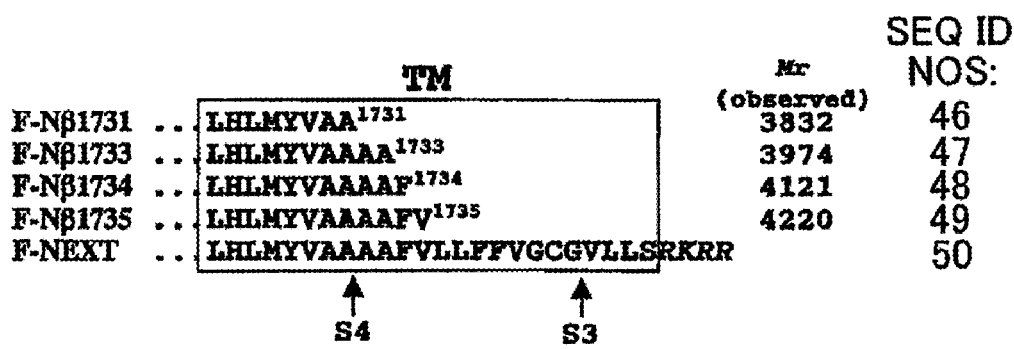
FIG. 6B shows Nβ species whose secretion is relatively increased by the effect of Alzheimer's disease pathogenic presenilin mutants.
Figure 6C:
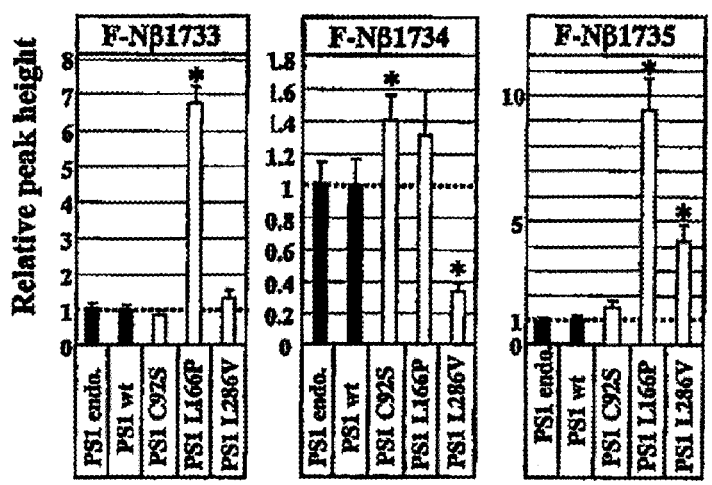
FIG. 6C shows the result of a semiquantitative analysis of the relative increase of their secretion.

K293 cells expressing wild-type (wt) PS1 or PS1 mutants associated with FAD, namely, PS1 C92S, PS1 L166P, and PS1 L286V, were stably transfected with F-NEXT. Then, the culture media of the cells expressing PS1 derivatives and F-NEXT were analyzed by MALDI-TOF MS, in order to examine the change in C-termini of F-Nβs. As shown in FIG. 6A, in contrast to the cells expressing wild-type PS1, characteristic change in a proteolysis pattern of C-termini of Nβs was observed in the cells expressing PS1 mutations associated with FAD. In particular, the cells expressing the PS1 L166P mutation causing a significant increase in Aβ42 production demonstrated a tendency to elongate F-Nβ peptides, and an increase in the production of F-Nβ species (F-Nβ 1733 and F-Nβ 1735) that were longer than F-Nβ1731 by 2 and 4 amino acid residues, respectively, was confirmed (see FIG. 6B). Furthermore, as shown in FIG. 6A, an increase in F-Nβ 1734 level was observed in the PS1 C92S cells, whereas an increase in F-Nβ 1735 level and a decrease in F-Nβ 1734 level were observed in the PS1 L286V cells. These results demonstrate that FAD pathogenic mutations affects a pattern of the S4 cleavage site so that the S4 cleavage site tends to shift toward the C-terminal side, thereby causing elongation of released peptides. Similarly to Aβ42, the aggressive PS1 L166P mutation affects the length of F-Nβs most significantly. It has been known that PS1 L166P mutation causes FAD during the young adult years. These effects were not specific to K293 cells, and the same effects of the PS mutations associated with FAD also were confirmed when using Neuro 2a cells (data not shown). Therefore, it can be said that every type of FAD pathogenic mutation affects the C-terminus of F-Nβ (see FIG. 6C).

Example 6

Effect of Proteolysis at S3 upon Efficiency of Proteolysis at S4

In order to examine the correlation between two cleavages occurring in a cell membrane, i.e., proteolysis at S4 that produces a Notch-β peptide and proteolysis at S3 that produces NICD determining signal transduction level, a mutant in which proteolysis at S3 is inhibited was prepared in the present example and it was confirmed using this mutant that there is no change in a S4 cleavage efficiency even in the case where a S3 cleavage efficiency is decreased artificially.

Figure 8A:
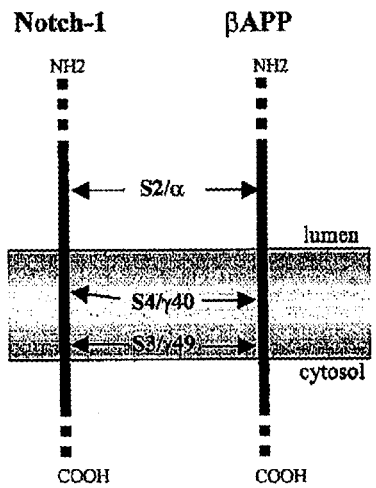
FIG. 8A illustrates how cleavages occur in transmembrane domains of Notch-1 and βAPP.
Figure 8B:
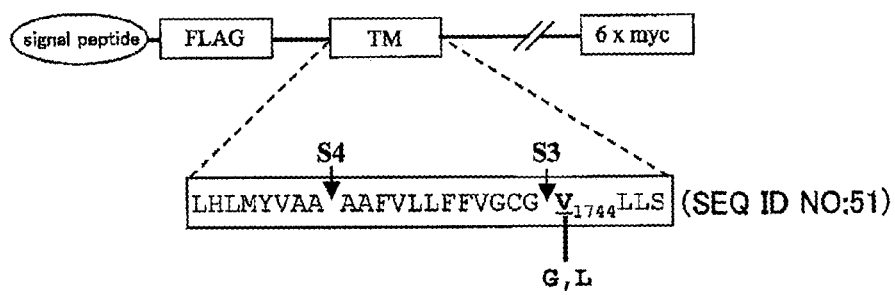
FIG. 8B is a schema specifically illustrating F-NEXT V1744G and F-NEXT V1744L mutants.

It has been reported that partial inhibition of S3 cleavage is caused by mutating V1744 of Notch-1 that resides on a C-terminal side with respect to a S3 cleavage site (Schroeter et al., Nature, 1998). Thus, at first, the change in a S4 cleavage activity caused by the inhibition of S3 cleavage was examined. In order to efficiently detect the products resulting from intramembranous endoproteolysis, NEXT analogues were FLAG tagged at their N-termini and myc-tagged at their C-termini. Thereafter, valine 1744 of the plasmid expressing the analogues (F-NEXT; Okochi, 2002) was mutated into glycine or leucine (hereinafter these mutants are referred to as F-NEXT V1744G and F-NEXT V1744L, respectively) (FIG. 8B). An F-NEXT expressing construct with or without S3 cleavage site mutation was stably transfected into K293 cells constantly expressing excessive wild-type PS1 or PS1 D385N lacking a γ-secretase function. The cells then were metabolically labeled with $^{35}$S methionine. Thereafter, newly radiolabeled F-Nβs and NICD present in the cell sediments and the corresponding culture media were detected by a method (IP-autoradiography) combining immunoprecipitation and radiation dosimetry performed after the separation by electrophoresis.

Figure 8C:
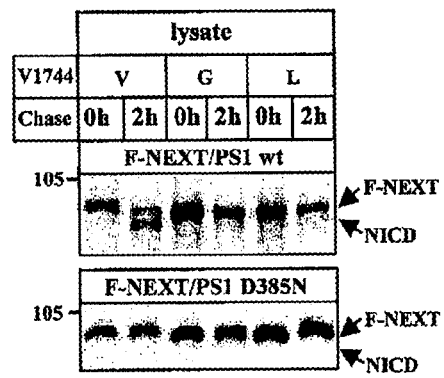
FIG. 8C is an electrophoretogram showing an example of inhibition of NICD production caused by mutating V1744.

The cell sediments were pulsed for 30 minutes, followed by IP-autoradiography with an anti-c-myc antibody (9E10). As a result, F-NEXT expression was observed. The cells were then chased for 2 hours. As a result, NICD production caused by the degradation of F-NEXT was observed, whereas NICD production was inhibited significantly in the V1744G and V1744L mutants (the upper panel of FIG. 8C). These results were in conformity with the conventional reports. Even in the case where the degradation of NICD was inhibited by adding Lactacystin as a proteasome inhibitor, the amount of radiolabeled NICD measured after a 2-hour chase was significantly small in the cells expressing V1744G and V1744L mutants. The intramembranous endoproteolysis and the NICD production caused by this F-NEXT were not at all observed in the PS1 D385N expressing cells (the lower panel of FIG. 8C). From these results, it can be said that the proteolysis shown in the upper panel of FIG. 8C was caused by PS/γ-secretase.

Figure 8E:
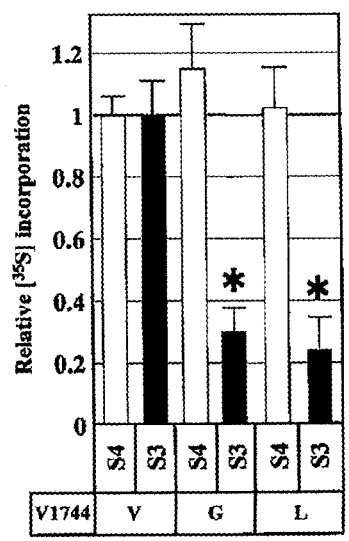
FIG. 8E shows the result of the measurement of S3 and S4 cleavage efficiencies in the cells.
Figure 8D:
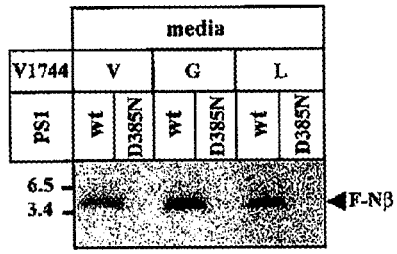
FIG. 8D is an electrophoretogram showing an example of F-Nβ secretion in the corresponding cell culture media.

Next, the culture media after a 2-hour chase were analyzed using an anti-FLAG antibody (M2). F-Nβs secreted from the F-NEXT V1744G mutant cells and the F-NEXT V1744L mutant cells were approximately the same level as those secreted from the wild-type F-NEXT cells (FIG. 8D). Furthermore, F-Nβ production was not observed in the cells expressing PS1 D385N mutant. From these results, it can be said that PS/γ-secretase affects this cleavage.

To further support the above-described conclusions, the S3 cleavage efficiency and the S4 cleavage efficiency were calculated. The ratio of NICD to F-NEXT analogues in the cell sediments and the ratio of F-Nβs in the culture media to the F-NEXT analogues in the corresponding cell sediments were determined. As a result, it was confirmed that although the V1744G mutant and the V1744L mutant both decrease the S3 cleavage activity in contrast to the wild-type PS1, they do not affect the S4 cleavage activity (FIG. 8E).

Example 7

Correlation between Decrease in S3 Cleavage Efficiency and Accuracy of S4 Cleavage In PS1 mutants that cause Alzheimer's disease, the change in accuracy of S4 cleavage occurs as well as a decrease in S3 cleavage activity. If the S3 cleavage is a precondition for the S4 cleavage, a decrease in S3 cleavage efficiency caused by a PS1 mutant should affect the accuracy of the S4 cleavage. Thus, in the present example, a S3 cleavage site mutant was prepared, and it was confirmed using this mutant that the accuracy of the S4 cleavage does not change even in the case where the S3 cleavage efficiency is decreased artificially.

Figure 9A:
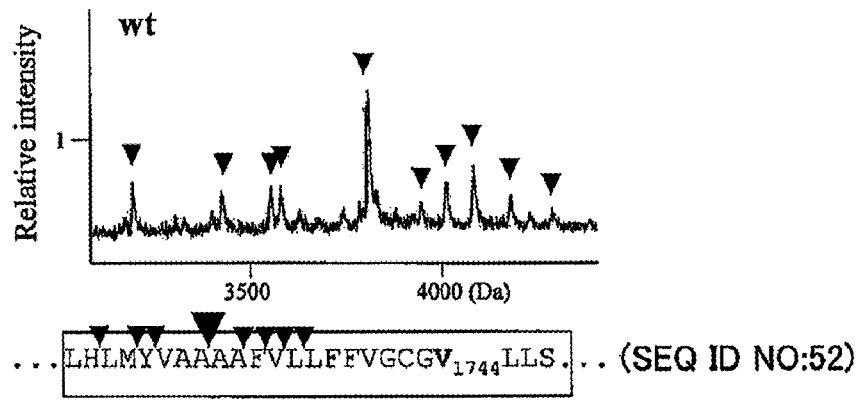
FIGS. 9A, 9B, and 9C are charts showing the result of mass spectroscopy with regard to F-Nβ peptides released from wild-type F-NEXT, F-NEXT V1744G mutant, and F-NEXT V1744L mutant, respectively.
Figure 9B:
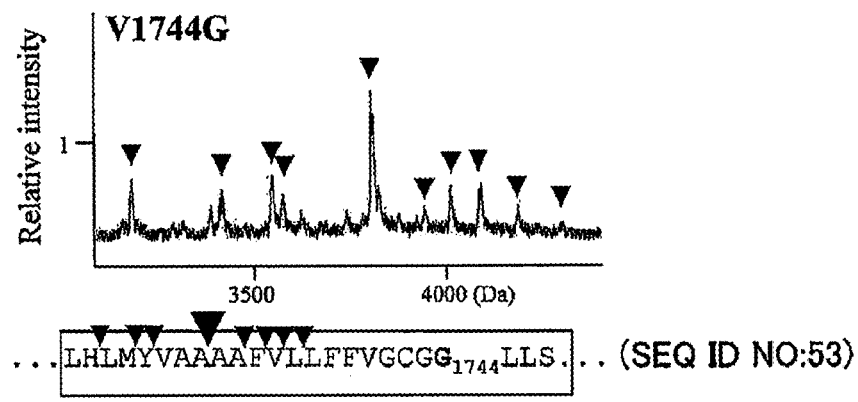
Figure 9C:
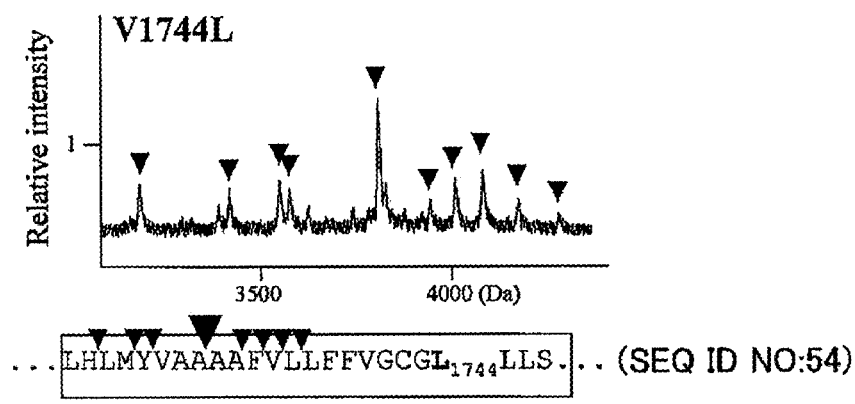

The cause of a familial Alzheimer's disease (FAD) is considered to be that FAD pathogenic PS mutants affect the accuracy of proteolysis by PS/γ-secretase and increase the production of Aβ42, which is elongated Aβ. Similarly, the FAD pathogenic PS mutants affect the accuracy of Notch cleavage by PS/γ-secretase and increase the production of elongated F-Nβ. Moreover, it has been reported that some of the PS mutants cause a decrease in S3 cleavage efficiency. Thus, the effect of S3 mutants that cause a decrease in S3 cleavage efficiency upon the accuracy of S4 cleavage was examined. F-Nβs contained in the culture media of the cells expressing wild-type F-NEXT, F-NEXT V1744G mutant, or F-NEXT V1744L mutant were immunoprecipitated with M2 agarose and then analyzed by MALDI-TOF MS. As a result, as shown in FIGS. 9B and 9C, the major cleavage site of the F-NEXT V1744G mutant and the F-NEXT V1744L mutant was between alanine 1731 and alanine 1732 as in the case of the wild type, and a pattern of several minor S4 cleavage sites located apart from each other were not at all affected by the mutations. In other words, it was confirmed that mutations that cause a decrease in S3 cleavage efficiency do not affect the accuracy of S4 cleavage at all. These data suggest that FAD pathogenic PS mutations indirectly affect the accuracy of S4 cleavage.

Example 8

Effect of Decrease in S4 Cleavage Efficiency upon S3 Cleavage Efficiency

Figure 10A:
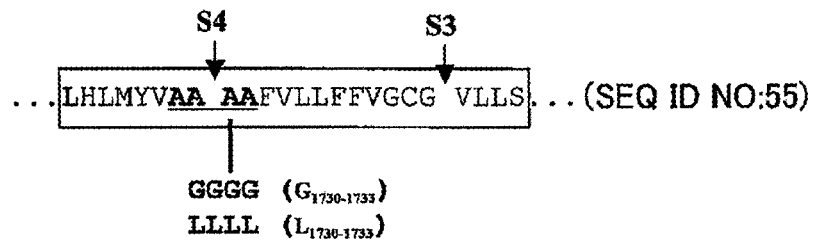
FIG. 10A is a schema specifically illustrating a S4 cleavage site mutant prepared in an example of the present invention.

Based on the assumption that S4 cleavage site mutation may exhibit a similar effect to that of the above-described artificially prepared S3 point mutants, the effect of a decrease in S4 cleavage efficiency upon a S3 cleavage efficiency was examined using F-NEXT G1730-1733 mutant and F-NEXT L1730-1733 mutant prepared by mutating four alanine residues around the S4 cleavage site into glycine residues and leucine residues, respectively (FIG. 10A). As a result, out of these two S4 cleavage site mutants, the F-NEXT L1730-1733 mutant with inhibited S4 cleavage activity exhibited a decrease in S3 cleavage efficiency. This result suggests that there is a proteolytic pathway through which NICD is produced by the S4 cleavage-dependent S3 proteolysis during intramembranous endoproteolysis of Notch-1.

Figure 10B:
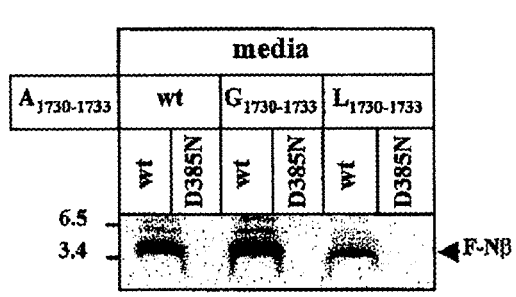
FIGS. 10B and 10C are examples of electrophretograms showing molecular weights of F-Nβs released from wild-type F-NEXT, F-NEXT G1730-1733 mutant, and F-NEXT L1730-1733 mutant, respectively.

Next, analysis also was made with regard to the assumption that the S4 cleavage site mutants similarly may affect the S4 cleavage. As indicated by the triangular arrowhead in FIG. 10A, a S4 cleavage site of Notch is in the center of four sequential alanine residues. The F-NEXT G1730-1733 mutant and the F-NEXT L1730-1733 mutant were prepared by mutating these four sequential alanine residues into glycine residues and leucine residues, respectively. These mutants then were subjected to the same pulse-chase experiment as that performed with respect to the S3 mutants. After a 2-hour chase, radiolabeled F-Nβs in the culture media were analyzed. As a result, F-β secretion was observed in the wild-type F-NEXT cells and the S4 mutated F-NEXT cells (FIG. 10B). However, although there was substantially no difference in the amount of F-Nβ production between the wild-type F-NEXT and the F-NEXT G1730-1733 mutant, the amount of F-Nβ production seemed to be decreased in the F-NEXT L1730-1733 mutant as compared with the wild-type F-NEXT (FIG. 10B).

Figure 10C:
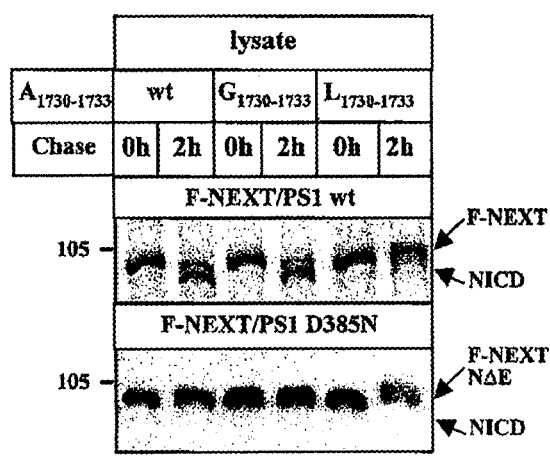

Next, production of radiolabeled NICD from F-NEXT contained in the corresponding cell sediments was analyzed. As a result, a similar level of NICD production to that of the wild-type F-NEXT cells was observed in the G1730-1733 mutant cells, whereas NICD production was decreased in the L1730-1733 mutant cells as compared with the cells expressing wild-type F-NEXT (the upper panel of FIG. 10C). These data suggest that S3 cleavage is inhibited in the L1730-1733 mutant.

Figure 10D:
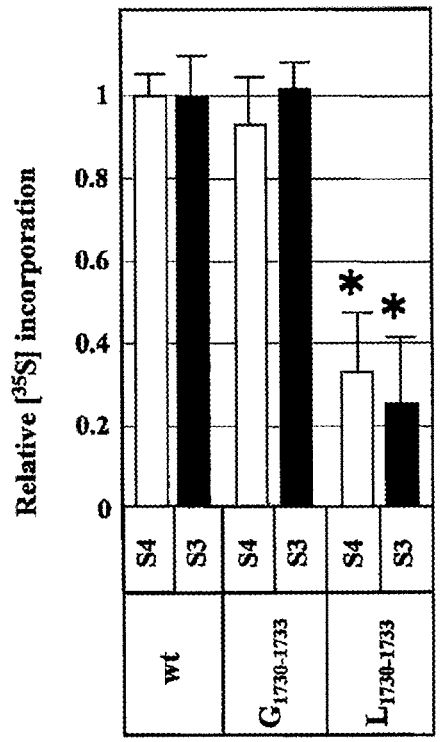
FIG. 10D shows the result of the measurement of S3 and S4 cleavage efficiencies in the cells.

In order to establish this result clearly, the S4 cleavage efficiency and the S3 cleavage efficiency were calculated in the same manner as in FIG. 8E. As a result, out of the two S4 mutants, the G1730-1733 mutant that hardly affected the S4 activity did not affect the S3 cleavage activity at all (FIG. 10D). In contrast, it was confirmed that the L1730-1733 mutant with inhibited S4 cleavage activity exhibited a decrease in S3 cleavage efficiency (FIG. 10D). Furthermore, from the facts that the PS/γ-secretase mechanism causes cleavage at both S3 and S4 and that no intermediate proteolysis product resulting from the S3 cleavage in close proximity to the cell membrane and the S4 cleavage at an approximate center of the transmembrane domain was found, it is considered the S3 cleavage and the S4 cleavage occur substantially at the same time. These results suggest that there is a proteolytic pathway through which NICD is produced by the S4 cleavage-dependent S3 proteolysis during intramembranous endoproteolysis of Notch-1.

Example 9

Correlation between S4 Cleavage Site and Activity

Figure 11A:
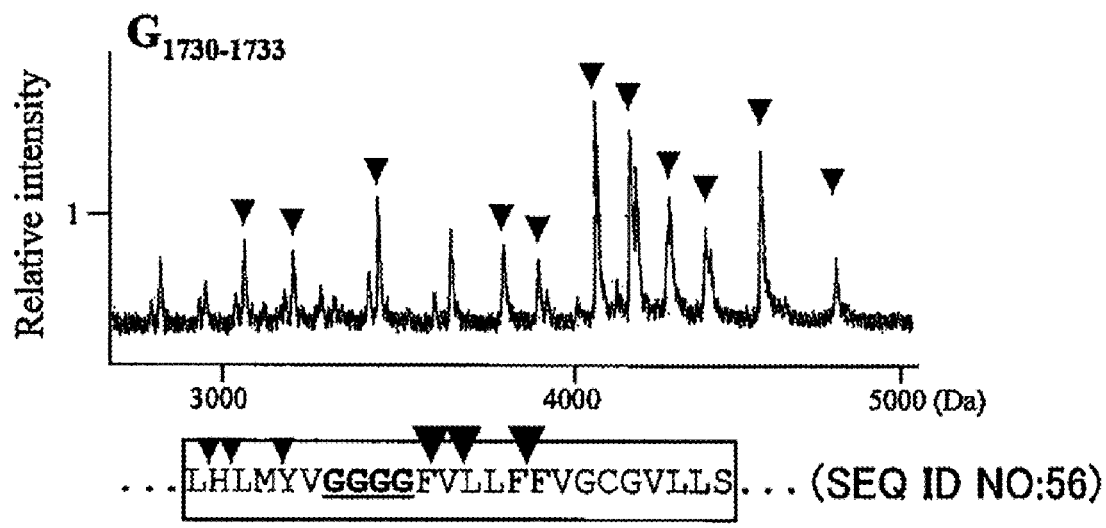
FIGS. 11A and 11B are charts showing the result of mass spectroscopy with regard to F-Nβ peptides released from F-NEXT G1730-1733 mutant and F-NEXT L1730-1733 mutant, respectively.
Figure 11B:
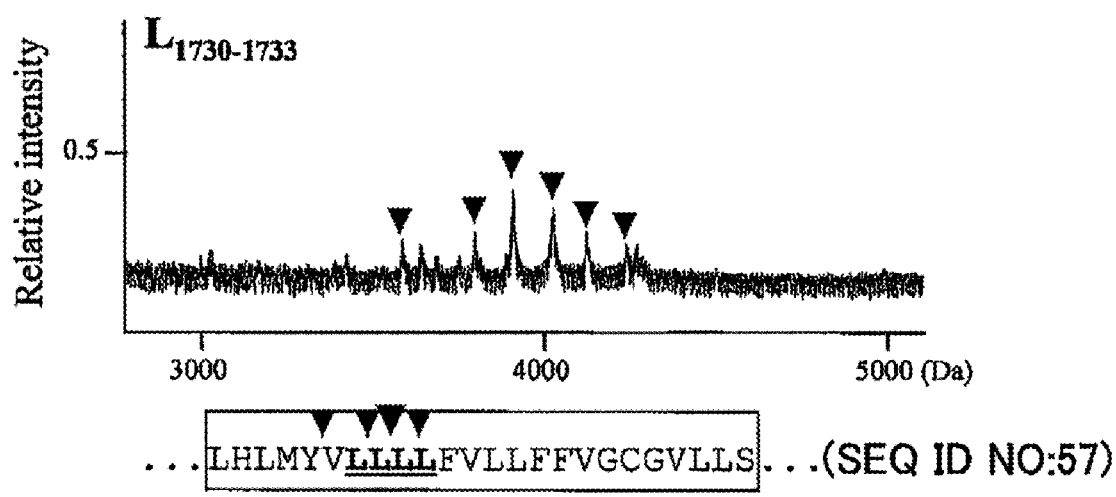

Subsequently, C-termini of F-Nβ G1730-1733 and F-Nβ L1730-1733 were determined. The amount of F-Nβs released from F-NEXT G1730-1733 substantially was equal to that released from the cell expressing wild-type F-NEXT (FIG. 1B). However, the G1730-1733 mutant did not have a S4 cleavage site between glycine 1731 and glycine 1732, as indicated by the inverse triangles in FIG. 11A. The major S4 cleavage sites of this mutant shifted toward the C-terminus of four sequential glycine residues to reside between phenylalanine 1734 and valine 1735, between valine 1735 and leucine 1736, and between phenylalanine 1738 and valine 1739, respectively. That is, S4 cleavage did not occur around the glycine residues, but minor cleavage sites were present apart from each other on the N-terminal side of the four glycine residues, so that MW of F-Nβs released from the F-NEXT G1730-1733 increased (FIG. 10B). Furthermore, as indicated by the inverse triangles in FIG. 11B, the F-NEXT L1730-1733 mutant had a major S4 cleavage site in the center of four sequential alanine residues, i.e., between leucine 1731 and leucine 1732, in the similar topology to that of the wild-type F-NEXT, and a minor cleavage site was hardly observed. Moreover, MW of F-Nβs released from the F-NEXT L1730-1733 mutant decreased (FIG. 10B).

INDUSTRIAL APPLICABILITY

As specifically described above, a novel polypeptide according to the present invention is derived from a Notch protein. In a series of proteolytic events of the Notch protein, the polypeptide is released to an extracellular space when NICD translocates to a nucleus as a result of intramembranous endoproteolysis that occurs subsequent to extracellular proteolysis. By using the novel polypeptide as a marker, it is possible to detect Notch signal transduction. Also, it is possible to detect cell differentiation, cell tumorigensis, apoptosis, Alzheimer's disease, etc., for example.

The invention claimed is:

1. An isolated or synthesized polypeptide consisting of the 20 amino acid sequence of at least one of SEQ ID NOs: 10 to 18.

\* \* \* \* \*